US010358408B2

(12) United States Patent
Thamatam et al.

(10) Patent No.: US 10,358,408 B2
(45) Date of Patent: Jul. 23, 2019

(54) SYNTHESIS OF AZELAIC ACID

(71) Applicant: POLYCARBON INDUSTRIES, INC., Newburyport, MA (US)

(72) Inventors: Rajesh Thamatam, Devens, MA (US); Bishwabhusan Sahoo, Devens, MA (US); Rajesh Shukla, Devens, MA (US)

(73) Assignee: POLYCARBON INDUSTRIES, INC., Newburyport, MA (US)

( * ) Notice: Subject to any disclaimer, the term of this patent is extended or adjusted under 35 U.S.C. 154(b) by 0 days.

(21) Appl. No.: 15/851,797

(22) Filed: Dec. 22, 2017

(65) Prior Publication Data

US 2019/0194115 A1    Jun. 27, 2019

(51) Int. Cl.
*C07C 51/38* (2006.01)
*C07C 51/353* (2006.01)
*C07C 51/09* (2006.01)

(52) U.S. Cl.
CPC .............. *C07C 51/38* (2013.01); *C07C 51/09* (2013.01); *C07C 51/353* (2013.01)

(58) Field of Classification Search
CPC ........ C07C 51/38; C07C 51/09; C07C 51/353
See application file for complete search history.

(56) References Cited

U.S. PATENT DOCUMENTS

| | | | | |
|---|---|---|---|---|
| 2,707,187 | A * | 4/1955 | Koehneke | C07D 209/08 548/469 |
| 2,729,674 | A | 1/1956 | McKinnis et al. | |
| 3,318,860 | A * | 5/1967 | Eichenbaum | C08F 110/00 502/114 |
| 5,380,928 | A | 1/1995 | Malek et al. | |
| 5,952,368 | A * | 9/1999 | Kertesz | C07D 207/333 514/423 |
| 2003/0010622 | A1 | 1/2003 | Moran, Jr. | |
| 2013/0131379 | A1 | 5/2013 | Lemaire et al. | |
| 2015/0119541 | A1* | 4/2015 | Eastham | C07C 51/38 526/273 |
| 2015/0158989 | A1* | 6/2015 | Cocquet | C08J 9/0061 521/59 |
| 2015/0183704 | A1 | 7/2015 | Alsters | |
| 2016/0145182 | A1 | 5/2016 | Dantale et al. | |

FOREIGN PATENT DOCUMENTS

JP    2002JP133250    12/2002

OTHER PUBLICATIONS

Gol'mov (Selective Malonic Synthesis, Zhurnal Obshchei Khimii, vol. 22, pp. 1944-1953, published 1952) (Year: 1952).*
Perkin (The Synthetical Formation of Closed Carbon-Chains. Part III. Some Derivatives of Pentamethylene, J. Chem. Soc., Trans, 51, pp. 240-248, Published 1887) (Year: 1887).*
Hydrolysis of esters (published Oct. 2016) (Year: 2016).*
Hydrolysis (Year: 2006).*
Krause (Octacidomycins, IV : A New Total Synthesis of rac-Octacidomycin and Structurally Related Oligocarboxylic Acids, Z. Naturforsch., B: Chem. Sci., 53, pp. 1043-1050, published 1998) (Year: 1998).*
Chembuddy pp. 1-3 (Year: 2005).*
Krause Translated p. 1-26 (Year: 1998).*
Gol'mov translated p. 1-29 (Year: 1952).*
V. P. Gol'mov, "Selective Malonic Syntheses" (Abstract), Zhurnal Obshchei Khimii (Russian Journal of General Chemistry) Journal, 1952, vol. 22, pp. 1944-1953, Springer International Publishing AG, Russia, ISSN: 0044-460X.
E. Antonelli et al., "Efficient Oxidative Cleavage of Olefins to Carboxylic Acids with Hydrogen Peroxide Catalyzed by Methyltrioctylammonium Tetrakis(oxodiperoxotungsto) phosphate (3−) under Two-Phase Conditions. Synthetic Aspects and Investigation of the Reaction Course," (Abstract) Journal of Organic Chemistry, 1998, vol. 63, pp. 7190-7206, American Chemical Society, Chicago, USA.
Mahboob, S.; "Studies in Structure and Amoebicidal Activity"; Oct. 1949; Abstract, pp. 2 and 135; Doctoral dissertation, University of London, UK.

* cited by examiner

*Primary Examiner* — Yevgeny Valenrod
*Assistant Examiner* — Blaine G Doletski
(74) *Attorney, Agent, or Firm* — Law Office of David Rucando; David Rucando

(57) ABSTRACT

This invention concerns a method of synthesizing Azelaic Acid. Particular reference is made to providing a new synthetic process for preparing azelaic acid in large scale with high purity (e.g., >99.7% with any individual impurity not more than 0.1%), which can be used as an active pharmaceutical ingredient.

20 Claims, No Drawings

SYNTHESIS OF AZELAIC ACID

FIELD OF THE INVENTION

This invention concerns a method of synthesizing Azelaic Acid.

BACKGROUND OF THE INVENTION

Azelaic acid is a saturated aliphatic dicarboxylic acid having the formula: HOOC—$(CH_2)_7$—COOH. It is also known as 1,9-nonanedioic acid.

Azelaic acid is used as a starting material for producing industrial products including polyesters, plasticizers and lubricants. Azelaic acid is also a component of hair- and skin-care products. See, R. H. Liu et al. "Azelaic acid in the treatment of papulopustular rosacea—A systematic review of randomized controlled trials," *Arch. Dermatol.*, (2006) 142 (8): 1047-1052. For example, Finacea® (azelaic acid) Gel, 15% (Bayer HealthCare Pharmaceuticals Inc. Whippany, N.J.) is prescribed for topical treatment of mild to moderate rosacea.

Large scale synthesis of azelaic acid remains challenging.

Industrially, azelaic acid is produced via ozonolysis of oleic acid followed by dioxygen oxidation, as described by B. Cornils et al. in "Dicarboxylic Acids, Aliphatic: Ullmann's Encyclopedia of Industrial Chemistry," Wiley (2010); and by E. F. Moran Jr. in "Process for making a C6 to C12 dibasic acid or azelaic acid using ozone generated from carbon dioxide," US 2003/0010622.

Other azelaic acid syntheses include those described in E. Antonelli et al., "Efficient Oxidative Cleavage of Olefins to Carboxylic Acids with Hydrogen Peroxide Catalyzed by Methyltrioctylammonium Tetrakis(oxodiperoxotungsto) phosphate (3-) under Two-Phase Conditions. Synthetic Aspects and Investigation of the Reaction Course" *J. Org. Chem.* 1998, 63, 7190-7206; Lemaire et al. in "Method for Preparing Carboxylic Acids by Oxidative Cleavage of a Vicinal Diol" US 2013/0131379; P. L. Alsters, "Process for the Preparation of (Azelaic) Acid from 9-Octadecenedioic Acid," US 2015/0183704; and S. Dantale et al. "Processes for Making Azelaic Acid and Derivatives Thereof" US 2016/0145182. These references and all publications cited herein are incorporated by reference in their entirety.

There is a need for new synthetic processes for preparing azelaic acid. Particularly, there is a need for viable, cost-effective, efficient scale-up procedures for manufacturing high purity azelaic acid under cGMP conditions for use as an active pharmaceutical ingredient.

BRIEF SUMMARY OF THE INVENTION

The present invention is directed to compositions and methods for synthesizing azelaic acid.

The invention provides a process for manufacturing azelaic acid comprising the step of decarboxylating heptane-1,1,7,7-tetracarboxylic acid with a mild base to form azelaic acid.

In one aspect, the mild base is an organic base. In some embodiments, the mild base is triethylamine, trimethylamine, methylamine, di-isopropyl ethylamine, diethylamine, propylamine, butylamine, tripropylamine, ethylmethylamine, ethylamine, diethylmethylamine, phenylamine, alanine, aniline, ammonia, dimethylaminopyridine or pyridine. In one embodiment the mild base is triethylamine.

In some embodiments the mild base is at a molar/molar ratio from about 0.6 to about 2.

In some embodiments the decarboxylation is performed using a solvent having a boiling temperature of at most about 200° C. In some embodiments the decarboxylation is performed at a temperature of at most about 200° C.

In certain embodiments the solvent is toluene, tetrahydrofuran, methyl tert-butyl ether, dimethylsulfoxide, acetonitrile, 1,2-dimethoxyethane, dioxane, benzene, xylenes, methyl t-butyl ether, methylene chloride, chloroform, methyl ethyl ketone, methyl isobutyl ketone, acetone, acetonitrile, benzene, N,N-dimethylformamide, N,N-dimethylacetamide, N-methylpyrrolidinone, hexane, heptane, or xylene.

In some embodiments the decarboxylation is performed in lab-scale, kilogram scale or plant-scale.

In some embodiments the azelaic acid is formed with a purity of at least about 90%.

The invention also provides a process for manufacturing azelaic acid comprising the steps of: hydrolyzing tetraethyl heptane-1,1,7,7-tetracarboxylate with an inorganic base to form heptane-1,1,7,7-tetracarboxylic acid; and decarboxylating the heptane-1,1,7,7-tetracarboxylic acid with a mild base thereby forming azelaic acid.

In some embodiments, the heptane-1,1,7,7-tetracarboxylic acid, resulting from the hydrolysis step, is isolated prior to the decarboxylating step. In some embodiments, the hydrolyzing step and the decarboxylating step are performed in situ.

In some embodiments, the inorganic base is sodium hydroxide, potassium hydroxide, lithium hydroxide, potassium carbonate, cesium carbonate, potassium phosphate, sodium carbonate, sodium phosphate, sodium ethoxide, or potassium tert-butoxide. In some embodiment, the inorganic base is sodium hydroxide. In one embodiment, the inorganic base is at a molar/molar ratio from about 1 to about 4.

In some embodiments, the hydrolysis is performed using a solvent having a boiling temperature of at most about 100° C. In some embodiments, the hydrolysis is performed using THF, toluene, methanol, dioxane, water, or mixtures thereof.

In some embodiments, the hydrolysis is performed at ambient temperature.

The invention also provides a process for manufacturing azelaic acid comprising the steps of: reacting 1,5-dibromopentane with diethylmalonate to form tetraethyl heptane-1,1,7,7-tetracarboxylate; hydrolyzing the tetraethyl heptane-1,1,7,7-tetracarboxylate with an inorganic base to form heptane-1,1,7,7-tetracarboxylic acid; and decarboxylating the heptane-1,1,7,7-tetracarboxylic acid with a mild base to form azelaic acid.

DETAILED DESCRIPTION OF THE INVENTION

The present invention provides several advantages over prior syntheses of azelaic acid.

(i) The present invention provides more mild processes for producing azelaic acid. In one aspect, the process comprises a mild decarboxylation step. In another aspect, the process comprises a mild hydrolysis step. In one embodiment, the decarboxylation step uses a mild base. In one nonlimiting example, the decarboxylation step uses an organic base such as trimethylamine as a very mild base compared to the previous use of strong acids. In another embodiment, the decarboxylation step uses a mild temperature. In one nonlimiting example, the decarboxylation step uses a solution of toluene refluxed between about 100° C. and about 110° C., which is much milder than other reports of very high temperature of >200° C.

(ii) The present invention provides a safer process. The process is safer because reaction conditions such as lower temperatures (e.g., <200° C.) are less hazardous and therefore less risky. Furthermore, the milder processes of the present invention are less damaging to manufacturing equipment.

(iii) The present invention provides more cost-effective processes because raw-materials are inexpensive and readily available. Furthermore, the processes do not require special equipment, such as equipment for cryogenic conditions or high-pressure conditions.

(iv) The present invention provides an industrially viable scale up because batches can be consistently scaled to kilogram-scale (e.g., 100 kg-200 kg) and plant-scale (e.g., <1,000 kg).

(v) The present invention provides processes that apply to Good Manufacturing Practice (GMP) and Good Laboratory Practice (GLP) conditions.

(vi) The present invention provides processes for producing azelaic acid in higher yield.

(vii) The present invention provides processes for producing azelaic acid in higher purity.

The term "azelaic acid" shall mean 1,9-nonanedioic acid, which has Chemical Abstracts Service (CAS) Registry Number: 123-99-9. Azelaic acid is also known as 1,7-heptanedicarboxylic acid. Azelaic acid has the formula: $HOOC-(CH_2)_7-COOH$ and is illustrated by the following chemical structure (I):

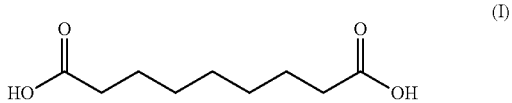 [SMILES: O=C(O)CCCCCCCC(=O)O]

Azelaic acid shall include, but not be limited to, salts, isoforms, isotopes, and formulations thereof.

Non-limiting examples of azelaic acid salts can include its disodium salt or ammonium salt. Non-limiting examples of isotopes of azelaic acid may have the replacement of hydrogen by deuterium or tritium, or have the replacement of a carbon by a $^{11}C$-, $^{13}C$- or $^{14}C$-enriched carbon. Non-limiting examples of azelaic acid esters are methyl, ethyl and other alkylesters.

Decarboxylation of Tetraacid

One aspect of the present invention comprises a step of decarboxylating heptane-1,1,7,7-tetracarboxylic acid (Formula III; tetraacid) to form azelaic acid (I).

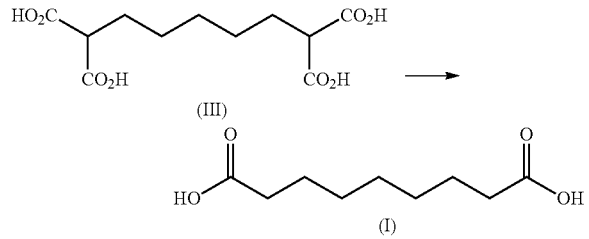

Decarboxylation Base

The decarboxylation step uses any suitable base. In some embodiments, the decarboxylation step uses any suitable mild base. In some embodiments, the suitable mild base has a pKb of about 10 or less. In some embodiments, the suitable mild base has a pKb of less than 10 (pKb<10). In some embodiments, the mild base is an organic base.

Examples of organic bases, include but are not limited to, triethylamine (TEA, $Et_3N$), trimethylamine, methylamine, di-isopropyl ethylamine (DIPEA), diethylamine, propylamine, butylamine, tripropylamine, ethylmethylamine, ethylamine, diethylmethylamine, phenylamine, alanine, aniline, ammonia, dimethylaminopyridine (DMAP) or pyridine. In one particular embodiment, the base is triethylamine. In another particular embodiment, the base is DIPEA. In another particular embodiment, the base is pyridine.

The step of decarboxylating the tetraacid can be performed using a stoichiometric amount of bases with respect to carboxylic acids. In one embodiment, the decarboxylation step can be performed using any effective molar ratio of bases greater than the acid number of the tetraacid. In one embodiment, a base is added to the reaction solution at a molar/molar ratio between about 0.5 and about 4.0. In another embodiment, a base is added to the reaction solution at a molar/molar ratio between about 0.6 and about 2.0. In another embodiment, triethylamine is added to the reaction solution at a molar/molar ratio between about 0.6 and about 2.0.

Decarboxylation Solvent

The step of decarboxylating the tetraacid, can be performed using any one or more suitable solvents.

In one embodiment, suitable solvents or solutions comprising one or more suitable solvents, have boiling temperatures below about 200° C. In another embodiment, suitable solvents or solutions have boiling temperatures below about 150° C.

In one embodiment, the organic solvent is an aprotic solvent. Examples of suitable solvents include, but are not limited to, toluene, tetrahydrofuran (THF), methyl tert-butyl ether (MTBE), dimethylsulfoxide, acetonitrile, 1,2-dimethoxyethane, dioxane, benzene, xylenes, methyl t-butyl ether, methylene chloride, chloroform, methyl ethyl ketone, methyl isobutyl ketone, acetone, acetonitrile, benzene, N,N-dimethylformamide, N,N-dimethylacetamide, or N-methylpyrrolidinone, hexane, heptane, or xylene.

In one particular embodiment, the organic solvent is toluene. In another particular embodiment, the organic solvent is THF. In another particular embodiment, the organic solvent is MTBE. In another particular embodiment, the organic solvent is xylene. In another particular embodiment, the solution comprises a combination of two or more solvents selected from THF, MTBE, and Xylene.

Decarboxylation Temperature

The step of decarboxylating the tetraacid, can be performed using any suitable temperature. In one aspect, a suitable temperature is a mild temperature. In one embodiment, the decarboxylation is performed at a temperature of at most about 200° C. In another embodiment, the decarboxylation is performed at a temperature of at most about 150° C. In another embodiment, the decarboxylation is performed at a temperature of at most about 110° C. In another embodiment, the decarboxylation is performed at a temperature of at most about 66° C. In another embodiment, the decarboxylation is performed at a temperature of at most about 55° C.

In another embodiment, the decarboxylation is performed at reflux temperature. In another embodiment, the decarboxylation is performed at the reflux temperature of a reaction solution comprising toluene, xylene, heptane, THF, or MTBE.

In another embodiment, the decarboxylation is performed at a temperature ranging from about 60° C. to about 100° C.

In another embodiment, the decarboxylation is performed at a temperature ranging from about 100° C. to about 200° C. In another embodiment, the decarboxylation is performed at a temperature ranging from about 110° C. to about 130° C. In another embodiment, the decarboxylation is performed at a temperature ranging from about 100° C. to about 120° C. In another embodiment, the decarboxylation is performed at a temperature ranging from about 80° C. to about 120° C.

In another embodiment, the decarboxylation is performed at about 110° C. In another embodiment, the decarboxylation is performed at about 66° C. In another embodiment, the decarboxylation is performed at about 55° C.

Decarboxylation Time

The tetraacid decarboxylation step can be performed using any suitable effective amount of time. A suitable amount of time can be any time needed for reaction completion.

In one embodiment, the effective amount of time ranges from about 2 to about 24 hours. In another embodiment, the effective amount of time it is between about 2 and about 18 hours. In another embodiment, the effective amount of time is between about 2 and about 12 hours. In another embodiment, the effective amount of time is between about 2 and about 6 hours. In one particular embodiment, the reaction time is about 15 hours. In another particular embodiment the reaction time is about 12 hours.

Decarboxylation Yield

The present invention provides processes for producing azelaic acid in high yield. In one aspect, the invention provides processes for producing azelaic acid in high purified yield.

In one embodiment the yield of azelaic acid from the decarboxylation step ranges from about 30% to about 50%. In another embodiment the yield of azelaic acid from the decarboxylation step ranges from about 40% to about 60%. In another embodiment the yield of azelaic acid from the decarboxylation step ranges from about 50% to about 70%. In another embodiment the yield of azelaic acid from the decarboxylation step ranges from about 60% to about 80%. In another embodiment the yield of azelaic acid from the decarboxylation step ranges from about 70% to about 90%. In another embodiment the yield of azelaic acid from the decarboxylation step ranges from about 80% to about 100%.

In one embodiment the yield of azelaic acid from the decarboxylation step is greater than about 40%. In another embodiment the yield of azelaic acid from the decarboxylation step is greater than about 70%. In another embodiment the yield of azelaic acid from the decarboxylation step is greater than about 80%. In another embodiment the yield of azelaic acid from the decarboxylation step is greater than about 90%.

In one embodiment the yield of azelaic acid from the decarboxylation step is about 40%. In another embodiment the yield of azelaic acid from the decarboxylation step is about 70%. In another embodiment the yield of azelaic acid from the decarboxylation step is about 80%. In another embodiment the yield of azelaic acid from the decarboxylation step is about 90%.

Hydrolysis of Tetraester

Another aspect of the present invention comprises a step of hydrolyzing tetraethylheptane-1,1,7,7-tetracarboxylate (Formula II; tetraester) to form heptane-1,1,7,7-tetracarboxylic acid (Formula III; tetraacid).

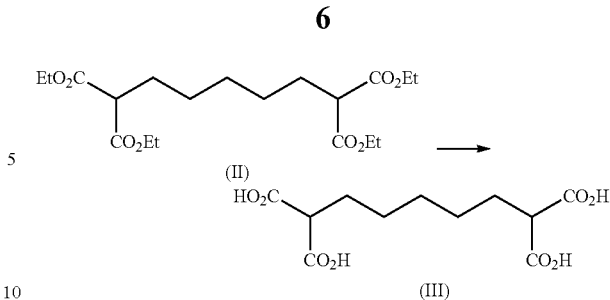

Hydrolysis Base

In some embodiments, the hydrolyzation step uses any suitable base. In some embodiments, the hydrolyzation step uses an inorganic base. In one embodiment, the base is sodium hydroxide, potassium hydroxide, lithium hydroxide, potassium carbonate, cesium carbonate, potassium phosphate, sodium carbonate, sodium phosphate, sodium ethoxide, or potassium tert-butoxide. In one particular embodiment the base is sodium hydroxide. In another particular embodiment the base is potassium hydroxide. In another particular embodiment the base is sodium ethoxide.

The step of hydrolyzing the tetraester can be performed using a stoichiometric amount of bases with respect to esters. The step of hydrolyzing the tetraester can be performed using any effective molar ratio of base to tetraester. In one embodiment the effective molar ratio is a base molar ratio greater than one compared to the ester number.

The tetraester hydrolysis step can be performed using any suitable base. In one embodiment, the hydrolysis step uses a base with a molar ratio greater than about 4 with respect to the ester number. In another embodiment, the hydrolysis step uses a base with molar ratio greater than about 6 with respect to the ester number. In another embodiment, the hydrolysis step uses a base with molar ratio greater than about 8 with respect to the ester number.

In one embodiment, the base is at a molar/molar ratio from about 1 to about 8. In one embodiment, the base is at a molar/molar ratio from about 1 to about 4.

In one embodiment, the suitable base is sodium hydroxide with molar ratio greater than about 4 with respect to the ester number. In another embodiment, a suitable base is sodium hydroxide with molar ratio greater than about 6 with respect to the ester number. In another embodiment, a suitable base is sodium hydroxide with molar ratio greater than about 8 with respect to the ester number.

In one embodiment, the hydrolysis step uses a base with a molar ratio of about 4 to about 8 with respect to the ester number. In another embodiment, the hydrolysis step uses a base with molar ratio of about 4 to about 6 with respect to the ester number. In another embodiment, the hydrolysis step uses a base with molar ratio of about 6 to about 8 with respect to the ester number.

In one embodiment, the suitable base is sodium hydroxide with molar ratio of about 4 to about 8 with respect to the ester number. In another embodiment, a suitable base is sodium hydroxide with molar ratio of about 4 to about 6 with respect to the ester number. In another embodiment, a suitable base is sodium hydroxide with molar ratio of about 6 to about 8 with respect to the ester number.

In one embodiment, the hydrolysis step uses a base with a molar ratio of about 4 with respect to the ester number. In another embodiment, the hydrolysis step uses a base with molar ratio of about 6 with respect to the ester number. In another embodiment, the hydrolysis step uses a base with molar ratio of about 8 with respect to the ester number.

In one embodiment, the suitable base is sodium hydroxide with molar ratio of about 4 with respect to the ester number. In another embodiment, a suitable base is sodium hydroxide with molar ratio of about 6 with respect to the ester number. In another embodiment, a suitable base is sodium hydroxide with molar ratio of about 8 with respect to the ester number.

The tetraester hydrolysis step can be performed using medium having any suitable pH. In one embodiment the pH of the medium could be anything greater than about pH 8. In one embodiment the pH of the medium could be anything greater than about pH 7. In another embodiment the pH of the medium is greater than or equal to about pH 8. In another embodiment the pH of the medium is greater than about pH 8. In another embodiment the pH of the medium is about pH 7 to about pH 8. In another embodiment the pH of the medium is about pH 8 to about pH 9. In another embodiment the pH of the medium is about pH 9 to about pH 10.

Hydrolysis Solvent

The step of hydrolyzing the tetraester, can be performed using any one or more suitable solvents. In one embodiment, the hydrolysis is performed using a solvent having a boiling temperature of at most about 100° C. In one embodiment, the hydrolysis is performed using THF, toluene, methanol, dioxane, water, or mixtures thereof. In one embodiment, the hydrolysis is performed using a solution of THF and water. In another embodiment, the hydrolysis is performed using a solution of about 50% THF and about 50% water. In another embodiment, the hydrolysis is performed using a solution of about 40% THF and about 60% water. In another embodiment, the hydrolysis is performed using a solution of about 30% THF and about 70% water. In another, the hydrolysis is performed using a solution of about 20% THF and about 80% water.

Hydrolysis Temperature

The step of hydrolyzing the tetraester, can be performed using any suitable temperature. In one aspect, a suitable temperature is a mild temperature. In another aspect, a suitable temperature is ambient temperature.

In one embodiment, the hydrolysis is performed at a temperature of at most about 100° C. In one embodiment, the hydrolysis is performed at a temperature of at most about 65° C. In another embodiment, the hydrolysis is performed at a temperature of at most about 45° C. In another embodiment, the hydrolysis is performed at a temperature of at most about 25° C.

In another embodiment, the hydrolysis is performed at a temperature ranging from about 20° C. to about 25° C., about 40° C. to about 45° C., about 25° C. to about 65° C., or about 35° C. to about 55° C.

In another embodiment, the hydrolysis is performed at a temperature of about 25° C. In another embodiment, the hydrolysis is performed at a temperature of about 45° C. In one particular embodiment, the hydrolysis is performed at ambient temperature. In another particular embodiment, the hydrolysis is performed at reflux temperature.

Hydrolysis Time

The step of hydrolyzing the tetraester, can be performed using any suitable effective amount of time. A suitable amount of time can be any amount of time needed for substantial reaction completion.

In one embodiment, effective amount of time ranges from about 2 to about 24 hours. In another embodiment, between about 2 and about 18 hours. In another embodiment, the effective amount of time is between about 2 and about 12 hours. In another embodiment, the effective amount of time is between about 2 and about 6 hours. In one particular embodiment the reaction time is 15 hours. In another particular embodiment the reaction time is 12 hours.

Hydrolysis Yield

In one embodiment the yield of tetraacid from the hydrolysis step ranges from about 30% to about 50%. In another embodiment the yield of tetraacid from the hydrolysis step ranges from about 40% to about 60%. In another embodiment the yield of tetraacid from the hydrolysis step ranges from about 50% to about 70%. In another embodiment the yield of tetraacid from the hydrolysis step ranges from about 60% to about 80%. In another embodiment the yield of tetraacid from the hydrolysis step ranges from about 70% to about 90%. In another embodiment the yield tetraacid from the hydrolysis step ranges from about 80% to about 100%.

In one embodiment the yield of tetraacid from the hydrolysis step is greater than about 40%. In another embodiment the yield of tetraacid from the hydrolysis step is greater than about 70%. In another embodiment the yield of tetraacid from the hydrolysis step is greater than about 80%. In another embodiment the yield of tetraacid from the hydrolysis step is greater than about 90%.

In one embodiment the yield of tetraacid from the hydrolysis step is about 40%. In another embodiment the yield of tetraacid from the hydrolysis step is about 70%. In another embodiment the yield of tetraacid from the hydrolysis step is about 80%. In another embodiment the yield of tetraacid from the hydrolysis step is about 90%.

Isolation of Tetraacid

In one embodiment the tetraacid as it is isolated crude and not purified prior to the decarboxylation step. In another embodiment the tetraacid is isolated crude and purified prior to the decarboxylation step.

Purification

In one aspect, azelaic acid is extracted from the crude product and purified using an organic solvent. In another aspect, azelaic acid is purified using an organic solvent. In one aspect, azelaic acid is extracted from the crude product and purified using the same organic solvent or combination of solvents.

In some embodiments, crude azelaic acid is extracted from crude product from an organic solvent, a combination of organic solvents, or a combination of an organic solvent and water. Examples of organic solvents include, but are not limited to, ethyl acetate, isopropyl acetate, butyl acetate, isobutyl acetate, toluene, methyl t-butyl ether (MTBE), methyl isobutyl ketone, hexane, heptane, and xylene, or 1-propanol/water (at various ratios).

In some embodiments, azelaic acid is purified by crystallization from an organic solvent, a combination of organic solvents, or a combination of an organic solvent and water. Examples of organic solvents include, but are not limited to, ethyl acetate, isopropyl acetate, butyl acetate, isobutyl acetate, toluene, methyl t-butyl ether (MTBE), methyl isobutyl ketone, hexane, heptane, and xylene, or 1-propanol/water (at various ratios).

In other embodiments, crude azelaic acid is purified by chromatography.

Tetraacid Purity

In one aspect, the invention provides a process yielding tetra-acid with high purity. In another aspect, the invention provides a process yielding tetra-acid with high purity prior to purification from crude product. In one embodiment, the tetra-acid product has a purity of at least about 60%, at least about 70%, at least about 80%, at least about 90%, at least about 95%, or at least about 97%.

In one embodiment, the tetraacid product has a purity ranging from about 40% to about 60%. In one embodiment, the tetraacid product has a purity ranging from about 60% to about 70%. In one embodiment, the tetraacid product has a purity ranging from about 70% to about 80%. In one embodiment, the tetraacid product has a purity ranging from about 80% to about 90%. In one embodiment, the tetraacid product has a purity ranging from about 90% to about 100%. In one embodiment, the tetraacid product has a purity ranging from about 95% to about 99%. In one embodiment, the tetraacid product has a purity ranging from about 97% to about 99%.

In one embodiment, the tetraacid product has a purity of about 60%, about 70%, about 80%, about 90%, about 95%, about 97%, or about 99%.

Azelaic Acid Purity

In one aspect, the invention provides a process yielding azelaic acid with high purity. In another aspect, the invention provides a process yielding azelaic acid with high purity prior to purification from crude azelaic acid product. In one embodiment, the azelaic acid product has a purity of at least about 70%, at least about 80%, at least about 90%, at least about 95%, at least about 97%, or at least about 99%.

In one embodiment, the azelaic acid product has a purity ranging from about 40% to about 60%. In one embodiment, the azelaic acid product has a purity ranging from about 60% to about 70%. In one embodiment, the azelaic acid product has a purity ranging from about 70% to about 80%. In one embodiment, the azelaic acid product has a purity ranging from about 80% to about 90%. In one embodiment, the azelaic acid product has a purity ranging from about 90% to about 100%. In one embodiment, the azelaic acid product has a purity ranging from about 95% to about 99%. In one embodiment, the azelaic acid product has a purity ranging from about 97% to about 99%.

In one embodiment, the azelaic acid product has a purity of about 70%, about 80%, about 90%, about 95%, about 97%, or about 99%.

In another embodiment, the azelaic acid product has a purity of at least 99%. In another embodiment, the final azelaic acid product has a purity of at least 99.5%, at least 99.7%, or at least 99.9%.

In another embodiment, the azelaic acid product has a purity of about 99.5%, about 99.7%, about 99.9%, or about 100%.

In one embodiment each individual impurity is not more than 1%. In another embodiment each individual impurity is not more than 0.5%, not more than 0.2%, not more than 0.1%, not more than 0.01%, or not more than 0.001%.

In one particular embodiment, high purity is greater than 99% pure and each individual impurity is not more than 0.1%. In another embodiment, high purity is greater than 99% pure and each individual impurity is not more than 0.05%.

Scale of Synthesis

In one aspect of the present invention, the process is performed at any scale. In one aspect of the present invention, the process is a large-scale process. In a further aspect of the present invention, the process is a laboratory-scale process. In a further aspect of the present invention, the large-scale process is a kilogram-scale process. In a further aspect of the present invention, the large-scale process is a plant-scale process.

In some embodiments of the present invention, the process produces azelaic acid in kilogram-scale (kilo-scale). In one embodiment azelaic acid is produced on a scale of about 0.5 kg to about 10 kg. In another embodiment azelaic acid is produced on a scale of about 1 kg to about 10 kg.

In another embodiment azelaic acid is produced on a scale of at least about 0.5 kg. In another embodiment azelaic acid is produced on a scale of at least about 1 kg. In another embodiment azelaic acid is produced on a scale of at least about 5 kg.

In some embodiment of the present invention, the process produces azelaic acid in plant-scale. In one embodiment azelaic acid is produced on a scale of about 10 kg to about 1000 kg. In another embodiment azelaic acid is produced on a scale of about 10 kg to about 100 kg. In another embodiment azelaic acid is produced on a scale of about 100 kg to about 1000 kg.

In another embodiment azelaic acid is produced on a scale of at least about 10 kg. In another embodiment azelaic acid is produced on a scale of at least about 100 kg. In another embodiment azelaic acid is produced on a scale of at least about 200 kg. In another embodiment azelaic acid is produced on a scale of at least about 500 kg. In another embodiment azelaic acid is produced on a scale of at least about 1000 kg. In another embodiment azelaic acid is produced on a scale of at least about 2000 kg. In another embodiment azelaic acid is produced on a scale of at least about 5000 kg.

EXAMPLES

Examples are offered for illustrative purposes only, and are not intended to limit the scope of the present invention in any way.

Example 1

Synthesis of Tetraester—Kilo Scale

Diethylmalonate 10.6 kg was refluxed with sodium ethoxide under nitrogen atmosphere. While refluxing, 1,5-dibromopentane (5 kg) was added slowly and continued refluxing until the reaction completion. Reaction was quenched by adding MTBE and water and stirring the whole mixture. The organic (top) layer was separated and stored in a container. The aqueous (bottom) layer was extracted twice with MTBE. All MTBE layers were combined and washed with water. Organic MTBE (top) layer was separated and concentrated under reduced pressure until all solvents and residual diethylmalonate were distilled out to concentrated oil with quantitative yield (>95%).

Example 2

Synthesis of Tetraester—Plant Scale

Sodium ethoxide solution (740 Kg) was charged to the reactor. Diethylmalonate (520 Kg) was charged to the reactor slowly over a period of 30 minutes. Heated the batch to reflux for 30 minutes. Charged 1,5-dibromopentane (250 Kg) slowly. The batch was stirred at reflux ihour. The reaction was cooled to ambient temperature. MTBE and purified water were added. The batch was cooled down to below 10° C. and the MTBE layer was extracted. The process was repeated twice. The combined organic layers were washed with purified water and concentrated to a thick oil under reduced pressure removing the residual malonate and any solvents to get thick oil with quantitative yield (>95%).

Example 3

Hydrolysis of Tetraester—R&D Scale

Tetraester 50 g was charged to the reaction flask. THF 90 g and 100 g of sodium hydroxide (50% aqueous solution, w/w) solution were then charged to the flask. The batch was stirred at 30-50° C. overnight. After the reaction completion, the product was acidified with concentrated hydrochloric acid (20-36% HCl) to pH<2, extracted with ethyl acetate to get 35 g of the desired crude product. The crude tetraacid product can be purified after the distillation of the solvents under reduced pressure to get the pure product. The product was crystalized using organic ethyl acetate to yield a product having >90% purity.

Example 4

Hydrolysis of Tetraester—R&D Scale

Tetra ester 50 g was charged to the reaction flask. THF 90 g and 100 g of 50% sodium hydroxide solution were then charged to the flask. The batch was stirred at 30-50° C. overnight. After the reaction completion, the product was acidified with concentrated hydrochloric acid (20-36% HCl) to pH<2, extracted with ethyl acetate and or MTBE to get 35 g of the desired crude product. The crude product can be purified after the distillation of the solvents under reduced pressure to get the pure product. The product was crystalized using MTBE to yield a product having >90% purity.

Example 5

Hydrolysis of Tetraester—Kilo Scale

Tetra ester 7.6 Kg was charged to the reactor. THF 13.5 Kg and 15 Kg of 50% sodium hydroxide solution and water 10-20 Kg were charged to the reactor and stirred at 30-50° C. overnight. After the reaction completion, the product was acidified with concentrated hydrochloric acid (20-36% HCl) to pH<2, extracted with ethyl acetate and or MTBE to get the desired crude product. The crude product was purified after the distillation of the solvents under reduced pressure to get the 5.3 Kg pure tetraacid product.

Example 6

Hydrolysis of Tetraester—Plant Scale

Tetraester 85 Kg was charged to the reactor. THF 151 Kg and 168 Kg of 50% sodium hydroxide solution and water 224 Kg were charged to the reactor and stirred at 30-50° C. overnight. After the reaction completion, the product was acidified with concentrated hydrochloric acid (20-36% HCl) to pH<2, and extracted with ethyl acetate and or MTBE to get the desired crude product. The crude product can be purified after the distillation of the solvents under reduced pressure to get 60 Kg of the pure tetraacid product.

Example 7

Hydrolysis of Tetraester, Plant Scale

Tetraester (7100 Kg) is charged to the reactor. THF (14000 Kg) is added to the reactor. A 50% sodium hydroxide (28500 Kg) and water (13200 Kg) solution are then charged to the reactor. The reaction is stirred at 30-50° C. overnight. After the reaction completion, the product is acidified with concentrated hydrochloric acid (20-36% HCl) to pH<2, and extracted with ethyl acetate to get the desired crude product. The crude product is purified after the distillation of the solvents under reduced pressure to get 5100 Kg of the pure product.

Example 8

Decarboxylation of Tetraacid—Lab Scale

Tetraacid (30-40 g) from example 3 was charged to the flask. Charged toluene (420 g) and distilled off some to remove water from the reaction. Adjusted toluene and charged trimethylamine (66 g) to a reactor equipped with Dean-Stark apparatus and a refluxing condenser. Stirred the mixture vigorously under nitrogen atmosphere. Refluxed the reaction mixture for at least 12 hours. Stopped heating and allowed the reaction to cool to room temperature. Under vigorous mixing, adjusted the pH of the reaction to below 2. Allowed the reaction to cool to room temperature and then cooled the reaction to 0-10° C. Filtered the solids and washed twice with ice cold water. Collected the solids and dry in an oven at 35-45° C. until constant weight. The reaction yielded 20 g of azelaic acid.

Example 9

Decarboxylation of Tetraacid—Plant Scale

Tetraacid (55-70 Kg) from Example 6 was charged to a flask. Charged toluene (370 Kg) and distilled off some to remove water from the reaction. Adjusted toluene and charged trimethylamine (56 Kg) to a reactor equipped with Dean-Stark apparatus and a refluxing condenser. Stirred the mixture vigorously under nitrogen atmosphere. Refluxed the reaction mixture for at least 12 hours. Stopped heating and allowed the reaction to cool to room temperature. Under vigorous mixing, adjusted the pH of the reaction to below 2. Allowed the reaction to cool to room temperature and then cooled the reaction to 0-10° C. Filtered the solids and washed twice with ice cold water. Collected the solids and dried the solid in an oven at 35-45° C. until constant weight. The reaction yielded 35 Kg of azelaic acid.

Example 10

Decarboxylation of Tetraacid—Plant Scale

Tetraacid (500 Kg) is charged to a flask. Toluene (250 Kg) is added and some is distilled off to remove water from the reaction. Trimethylamine (730 Kg) is added to a reactor equipped with Dean-Stark apparatus and a refluxing condenser. The mixture is stirred vigorously under nitrogen atmosphere. The reaction mixture is refluxed for 12 hours. Heating is stopped, and the reaction is allowed to cool to room temperature. Under vigorous mixing, pH of the reaction is adjusted to below 2. The reaction is cooled to 0-10° C. The solids are filtered and washed twice with ice cold water. The solids are collected and dried in an oven at 35-45° C. until constant weight. The reaction yields 340 Kg of azelaic acid.

Example 11

Decarboxylation of Tetraacid—Plant Scale

Tetraacid (5000 Kg) is charged to a flask. Toluene (2500 Kg) is added and some is distilled off to remove water from the reaction. Trimethylamine (7320 Kg) is added to a reactor equipped with Dean-Stark apparatus and a refluxing condenser. The mixture is stirred vigorously under nitrogen atmosphere. The reaction mixture is refluxed for 12 hours. Heating is stopped, and the reaction is allowed to cool to room temperature. Under vigorous mixing, pH of the reaction is adjusted to below 2. The reaction is cooled to 0-10° C. The solids are filtered and washed twice with ice cold water. The solids are collected and dried in an oven at 35-45° C. until constant weight. The reaction yields 3406 Kg of azelaic acid.

Example 12

Purification of Azelaic Acid—R&D Lab Scale

Crude Azelaic acid (32 g) from example 8 and charcoal (3.2 g) were charged to the reactor. Ethyl acetate (175 Kg) was charged to the reactor and the reaction mixture was heated to reflux temperature. The hot solution was transferred through a cloth or paper filter. The filtrates to 0-10° C. The solids were filtered and washed twice with MTBE. The wet cake was dried under vacuum at NMT 50° C. to yield 29 g of azelaic acid (99% purity) with not more than 0.5% of other individual impurities.

Example 13

Purification of Azelaic Acid—Plant Scale

Crude Azelaic acid (32 Kg) from example 8 and charcoal (3.2 Kg) were charged to the reactor. Ethyl acetate (175 Kg) was charged to the reactor and the reaction mixture was heated to reflux temperature. The hot solution was transferred through a filter. The filtrates to 0-10° C. The solids were filtered and washed twice with MTBE. The wet cake was dried under vacuum at NMT 50° C. to yield 25 kg of azelaic acid (99% purity) with not more than 0.1% individual impurities.

Example 14

Purification of Azelaic Acid—Plant Scale

Crude azelaic acid (3200 Kg) and charcoal (320 Kg) are charged to the reactor. Ethyl acetate (1750 Kg) is then charged to the reactor. The batch mixture is heated to reflux temperature. The hot solution is then transferred through a filter. The filtrates are cooled to 10° C. The solids are filtered and washed twice with MTBE. The wet cake is dried under vacuum at NMT 50° C. to yield 2577 kg (97% purity).

What is claimed is:

1. A process for manufacturing azelaic acid comprising the step of:
   (a) decarboxylating heptane-1,1,7,7-tetracarboxylic acid with an organic amine base; thereby forming azelaic acid.

2. The process of claim 1, wherein the organic amine base is triethylamine, trimethylamine, methylamine, di-isopropyl ethylamine, diethylamine, propylamine, butylamine, tripropylamine, ethylmethylamine, ethylamine, diethylmethylamine, phenylamine, alanine, aniline, dimethylaminopyridine or pyridine.

3. The process of claim 1, wherein the organic amine base is triethylamine.

4. The process of claim 1, wherein the organic amine base is at a molar/molar ratio of bases with respect to carboxylic acids from about 0.6 to about 2.

5. The process of claim 1, wherein the decarboxylation is performed using a solvent having a boiling temperature of at most about 200° C.

6. The process of claim 1, wherein the solvent is toluene, tetrahydrofuran, methyl tert-butyl ether, dimethylsulfoxide, acetonitrile, 1,2-dimethoxyethane, dioxane, benzene, xylenes, methyl t-butyl ether, methylene chloride, chloroform, methyl ethyl ketone, methyl isobutyl ketone, acetone, acetonitrile, benzene, N,N-dimethylformamide, N,N-dimethylacetamide, N-methylpyrrolidinone, hexane, heptane, or xylene.

7. The process of claim 1, wherein the decarboxylation is performed at a temperature of at most about 200° C.

8. The process of claim 1, wherein decarboxylation is performed in lab-scale, kilogram scale or plant-scale.

9. The process of claim 1, wherein the azelaic acid is formed with a purity of at least about 90%.

10. The process of claim 1, wherein the decarboxylation is performed using a solvent, wherein the solvent is an aprotic solvent.

11. The process of claim 1, wherein the decarboxylation is performed at a temperature of at most about 110° C.

12. The process of claim 1, wherein the decarboxylation is performed at a temperature of at most about 66° C.

13. The process of claim 1, wherein the decarboxylation is performed at a temperature of at most about 55° C.

14. The process of claim 1, wherein the decarboxylation is performed at a temperature ranging from about 100° C. to about 110° C.

15. The process of claim 1, wherein the decarboxylation is performed at a temperature ranging from about 60° C. to about 100° C.

16. The process of claim 1, wherein the decarboxylation is performed at a temperature ranging from about 100° C. to about 200° C.

17. The process of claim 1, wherein the decarboxylation is performed at a temperature ranging from about 80° C. to about 120° C.

18. The process of claim 1, wherein the decarboxylation is performed using an effective molar ratio of bases greater than the acid number of the tetraacid.

19. The process of claim 1, wherein the organic base is at a molar/molar ratio of bases with respect to carboxylic acids between about 0.5 and about 4.0.

20. A process for manufacturing azelaic acid comprising the step of: decarboxylating heptane-1,1,7,7-tetracarboxylic acid using triethylamine in toluene at a temperature of about 100° C. to about 110° C.; thereby forming azelaic acid.

* * * * *

UNITED STATES PATENT AND TRADEMARK OFFICE
CERTIFICATE OF CORRECTION

PATENT NO. : 10,358,408 B2
APPLICATION NO. : 15/851797
DATED : July 23, 2019
INVENTOR(S) : Rajesh Thamatam, Bishwabhusan Sahoo and Rajesh Shukla Page 1 of 1

It is certified that error appears in the above-identified patent and that said Letters Patent is hereby corrected as shown below:

In the Specification

Column 12, Line 11:
Replace "trimethylamine" with -- triethylamine --

Column 12, Line 29:
Replace "trimethylamine" with -- triethylamine --

Column 12, Line 46:
Replace "trimethylamine" with -- triethylamine --

Column 12, Line 63:
Replace "trimethylamine" with -- triethylamine --

Signed and Sealed this
Tenth Day of September, 2019

Andrei Iancu
*Director of the United States Patent and Trademark Office*